US012676213B2

(12) United States Patent
Rabideau

(10) Patent No.: US 12,676,213 B2
(45) Date of Patent: Jul. 7, 2026

(54) TARGET-TO-CATALYST TRANSLATION NETWORKS

(71) Applicant: Syntensor, Inc., Burlington, VT (US)

(72) Inventor: Clayton Morrissey Rabideau, Richmond, VA (US)

(73) Assignee: Syntensor, Inc., Burlington, VT (US)

( * ) Notice: Subject to any disclaimer, the term of this patent is extended or adjusted under 35 U.S.C. 154(b) by 1073 days.

(21) Appl. No.: 17/771,137

(22) PCT Filed: Oct. 23, 2020

(86) PCT No.: PCT/US2020/057149
§ 371 (c)(1),
(2) Date: Apr. 22, 2022

(87) PCT Pub. No.: WO2021/081390
PCT Pub. Date: Apr. 29, 2021

(65) Prior Publication Data
US 2022/0383994 A1 Dec. 1, 2022

Related U.S. Application Data

(60) Provisional application No. 62/925,846, filed on Oct. 25, 2019.

(51) Int. Cl.
*G06N 3/08* (2023.01)
*G06N 3/063* (2023.01)
*G16C 20/70* (2019.01)

(52) U.S. Cl.
CPC ............. *G16C 20/70* (2019.02); *G06N 3/063* (2013.01); *G06N 3/08* (2013.01)

(58) Field of Classification Search
CPC .......... G16C 20/70; G16C 20/50; G06N 3/08; G06N 3/088; G16B 20/00; G16B 40/00
See application file for complete search history.

(56) References Cited

U.S. PATENT DOCUMENTS

| | | | | |
|---|---|---|---|---|
| 2020/0050737 A1* | 2/2020 | Kajino | ................... | G06F 40/16 |
| 2020/0082916 A1* | 3/2020 | Polykovskiy | .......... | G06N 3/045 |
| 2020/0320351 A1* | 10/2020 | Nikolenko | ........... | G06V 10/764 |
| 2022/0230713 A1* | 7/2022 | Maragakis | ........... | G06N 3/0475 |

OTHER PUBLICATIONS

Zak Costello et al.; How to Hallucinate Functional Proteins; Mar. 1, 2019; Cornell University Library; pp. 1-13 (Year: 2019).*

(Continued)

*Primary Examiner* — Phenuel S Salomon
(74) *Attorney, Agent, or Firm* — Dergosits & Noah LLP; Todd A. Noah

(57) ABSTRACT

The present invention provides a computer system for generating the molecular structure of a catalytic activator for a reaction in which input reactants, a.k.a. substrates, are converted into an output product, the computer system comprising: a trained machine learning model, preferably a variational autoencoder, configured to receive an operating feature set defining chemical features of the input reactants and chemical features of the output product of a reaction and to generate therefrom a set of catalyst features defining one or more catalytic activator, which is preferably an enzyme, for catalysing a reaction to convert the input reactants to the output product.

16 Claims, 6 Drawing Sheets

(56)     References Cited

OTHER PUBLICATIONS

International Search Report and Written Opinion in corresponding International Patent Application No. PCT/US2020/057149 dated Feb. 8, 2021.

Costello et al., "How to Hallucinate Functional Proteins," ARXIV. org, Cornell University Library, 201 Olin Library, Cornell University, Ithaca, New York, Mar. 1, 2019.

Kitchin, John R., "Machine learning in catalysis," Nature Catalysis, vol. 1, Apr. 16, 2018.

International Preliminary Report on Patentability from corresponding International Patent Application No. PCT/US2020/057149, dated Apr. 26, 2022.

\* cited by examiner

FIG. 5

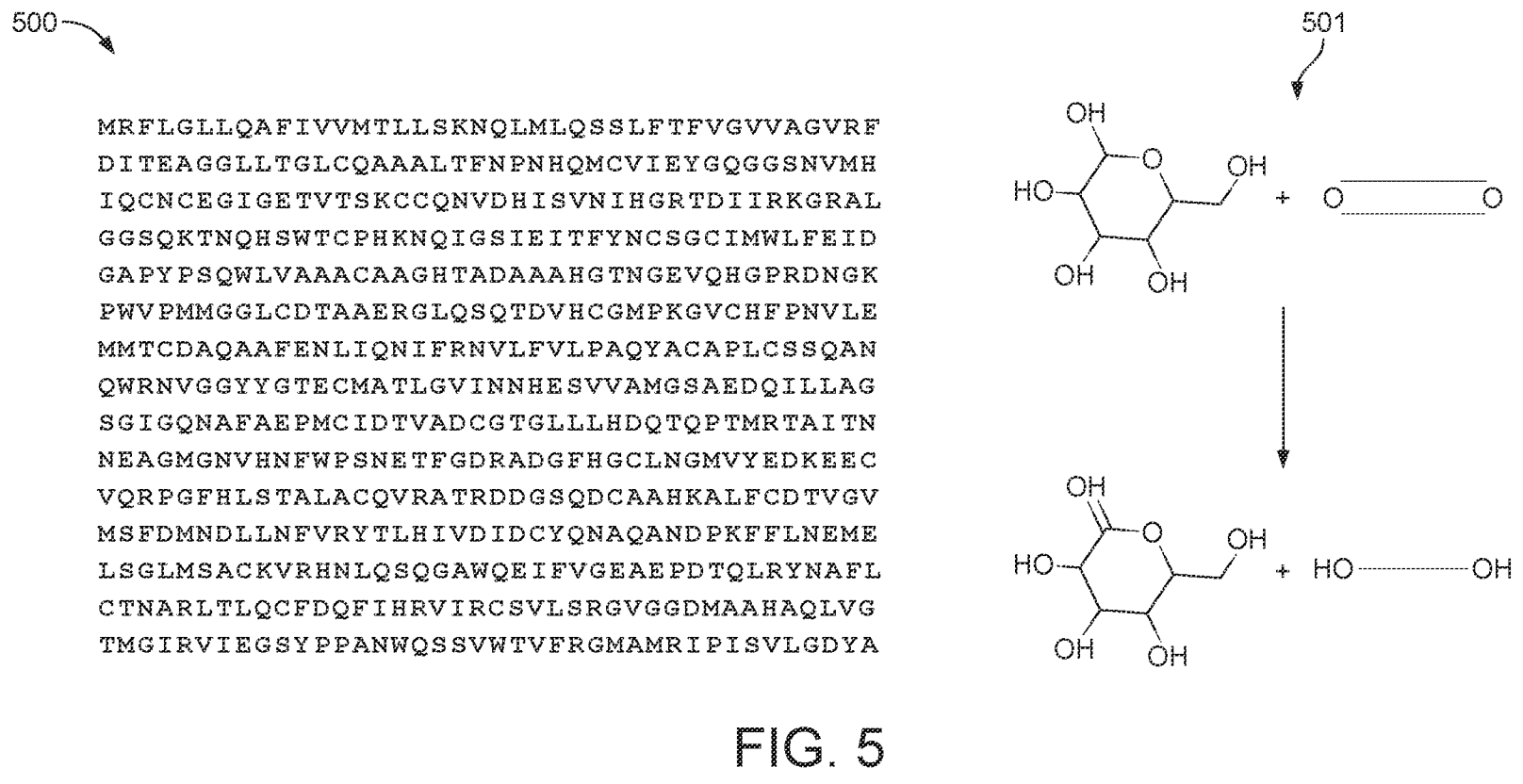

```
MRFLGLLQAFIVVMTLLSKNQLMLQSSLFTFVGVVAGVRF
DITEAGGLLTGLCQAAALTENPNHQMCVIEYGQGGSNVMH
IQCNCEGIGETVTSKCCQNVDHISVNIHGRTDIIRKGRAL
GGSQKTNQHSWTCPHKNQIGSIEITFYNCSGCIMWLFEID
GAPYPSQWLVAAACAAGHTADAAAHGTNGEVQHGPRDNGK
PWVPMMGGLCDTAAERGLQSQTDVHCGMPKGVCHFPNVLE
MMTCDAQAAFENLIQNIFRNVLFVLPAQYACAPLCSSQAN
QWRNVGGYYGTECMATLGVINNHESVVAMGSAEDQILLAG
SGIGQNAFAEPMCIDTVADCGTGLLLHDQTQPTMRTAITN
NEAGMGNVHNFWPSNETFGDRADGFHGCLNGMVYEDKEEC
VQRPGFHLSTALACQVRATRDDGSQDCAAHKALFCDTVGV
MSFDMNDLLNFVRYTLHIVDIDCYQNAQANDPKFFLNEME
LSGLMSACKVRHNLQSQGAWQEIFVGEAEPDTQLRYNAFL
CTNARLTLQCFDQFIHRVIRCSVLSRGVGGDMAAHAQLVG
TMGIRVIEGSYPPANWQSSVWTVFRGMAMRIPISVLGDYA
```

TARGET-TO-CATALYST TRANSLATION NETWORKS

FIELD OF THE INVENTION

The present disclosure generally relates to machine learning and reaction engineering via enzymatic catalysis.

The invention pertains to the generation of catalytic activators which are specific to a set of inputs and outputs. More specifically, the invention pertains to the generation of an enzymatic or other catalyst given a set of target input substrates and output product molecules such that the catalyst is generated algorithmically from that set of targets. In particular, the algorithm is constructed such that it comprises a Variational AutoEncoder which is further comprised of an encoder and decoder such that the latent space between the encoder and decoder is continuous.

BACKGROUND OF THE INVENTION

The global small organic molecule and specialty chemicals market has a marked impact on our planet, with even sub-markets such as pharmaceuticals having output of over 900 billion in 2017, with projections predicting an output of $1170 in 2021, growing at 5.8% annually. The pharmaceutical industry, along with its sibling industries, rely on cost-effective large-scale manufacturing of organic molecules. Small molecules are manufactured through the use of chemical synthesis. Chemical synthesis is a collection of steps to convert one molecule, a substrate, into a different molecule, a product, and it involves the addition, removal, re-arrangement, or other modification of atomic and/or energetic properties of the original molecule. Due to thermodynamic constraints such as activation energy, these conversions, also known as reactions, rarely proceed at useful rates without the influence of a catalyst. Catalysts are agents which increase the rate of reaction and which, in their most useful form, are specific to the reactants. This means that in their ideal form, catalysts will increase the rate of conversion between substrate(s) and product(s) compared to the conversion between those substrate(s) and product(s) in the absence of a catalyst, thereby potentially decreasing the cost of manufacturing of organic chemicals.

The engineering of these catalysts is a highly difficult task. This is especially true for catalysts which operate in physiological conditions. While there is an existing set of organic enzymatic catalysts generated through natural evolution, these are clustered around core metabolic or signaling functions, leaving the vast majority of the estimated $10^{60}$-$10^{63}$ possible small molecule organic chemicals unreachable.

A similar problem exists for enzymatic or other catalysts that are generated manually or through directed evolution. These mechanisms for generating new catalysts require a large investment of both capital and time, meaning that the construction of new catalysts is limited to a small subset of possible applications.

Most prior work can be categorized as either a manual modeling or directed evolution approach to designing novel enzymes. These methods are limited in applicability and effectiveness. Manual modeling of enzyme structure via molecular dynamics or other simulations is problematic because the function connecting enzyme sequence and catalytic properties is not being solved for directly. This has the effect of requiring manual intervention for each new enzyme, greatly increasing cost and reducing scalability. On its own, directed evolution also requires expensive manual intervention in order to choose candidate enzymes.

OBJECTS OF THE INVENTION

It is an object of this invention to generate catalysts from a set of chemical features.

It is another object of this invention to achieve this generation in such a way that a catalyst could be generated from any set of chemical features which are comprised of small organic molecules.

It is yet another object of this invention that multi-task learning be applied to the translation of chemical features to catalyst features and vice versa.

Other objectives and advantages of the invention will in part be obvious and will in part be apparent from the specification and drawings.

SUMMARY OF THE INVENTION

In order to overcome the constraints imposed by manual modeling or directed evolution as means of generating catalysts, we use generative modeling to construct catalyst features given a set of chemical features comprised of reactant and product features.

This generative model is constructed by training Variational AutoEncoders on both sets of features such that their respective latent space manifolds are jointly distributed. This results in a latent vector generated from a chemical encoder being similar or identical to a latent vector generated from a catalyst encoder. Correspondingly, a latent vector generated from a chemical encoder can be decoded by a catalyst decoder to find the corresponding catalyst for that set of chemical features and vice-versa. This method of solving for the joint distribution is also known as multi-task learning.

The invention accordingly comprises the several steps and the relation of one or more of such steps with respect to each of the others, and the apparatus embodying features of construction, combinations of elements and arrangement of parts that are adapted to affect such steps. All is exemplified in the following detailed disclosure, and the scope of the invention will be indicated in the claims.

In particular, in a first aspect a computer system is provided, wherein the computer system is for generating the molecular structure of a catalytic activator for a reaction in which input reactants, a.k.a. substrates, are converted into an output product, the computer system comprising:

a trained machine learning model configured to receive an operating feature set defining chemical features of the input reactants and chemical features of the output product of a reaction and to generate therefrom a set of catalyst features defining one or more catalytic activators for catalysing a reaction to convert the input reactants to the output product.

In a second aspect a method of training a Variational AutoEncoder machine learning model is provided, the method comprising:

providing a first set of training data defining chemical features of input reactants and output products for each of a plurality of reactions, encoding the chemical features into latent vectors defining points in a latent space and defining the distribution of the latent vectors in the latent space, providing a second set of training data defining catalyst features of catalytic activators for each of the plurality of reactions, encoding the catalyst features into catalyst latent vectors in the latent space and matching the distribution of the catalyst latent vectors to the chemical latent vectors such that decoding a chemical latent vector at a point in the latent space generates catalyst features of a catalytic activator for catalysing a reaction to convert the input reactants of that reaction to an output product, the input reactant and the output product defined by the chemical features encoded in the latent vector.

In a third aspect a method is provided for generating the molecular structure of a catalytic activator for a reaction in which input reactants, a.k.a. substrates, are converted into an output product, the method comprising inputting into a trained machine learning model of the computer system of the first aspect described above an operating feature set defining chemical features of the input reactants and chemical features of the output product of a reaction, and obtaining therefrom a set of catalyst features defining one or more catalytic activators for catalysing a reaction to convert the input reactants to the output product.

In a fourth aspect a method is provided comprising making the one or more catalytic activators defined by the method according to the third aspect above, and optionally performing the reaction to convert the input reactants to the output product using the one or more catalytic activators.

Preferably in the above aspects the catalytic activator is a catalyst. More preferably the catalytic activator is an enzyme.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter. Nor is the claimed subject matter limited to implementations that solve any or all of the disadvantages noted herein.

BRIEF DESCRIPTION OF THE DRAWINGS

For a more complete understanding of the invention, reference is made to the following description and accompanying drawings, in which:

FIG. 5 An example of a generated sequence of amino acids, in this case an enzyme generated from reaction features for the oxidation of glucose to hydrogen peroxide and D-glucono-1,5-lactone.

DETAILED DESCRIPTION OF THE INVENTION

Figure 1:
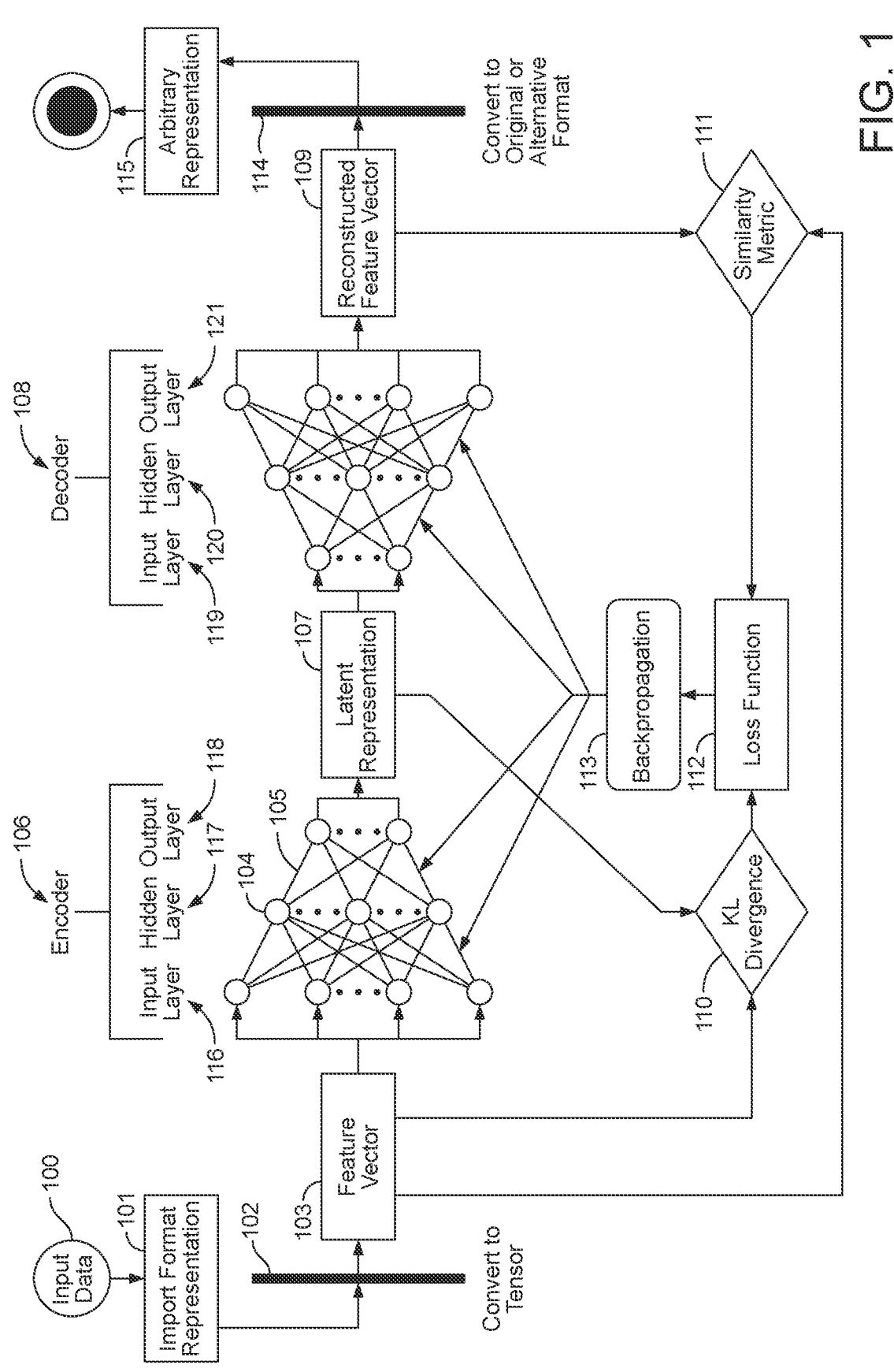
FIG. 1 Detailed depiction of a Variational AutoEncoder for amino acid sequences.

As described above, the present invention aims to address the problem of how to engineer catalysts.

What is needed is a mechanism by which the function that connects any given reaction to a set of catalyst features can be determined from a model of that function which is derived from a set of examples.

Machine Learning—https://patents.google.com/patent/WO2017031357A1/en

Machine learning relates to methods and circuitry that can learn from data and make predictions based on data. In contrast to methods or circuitry that follow static program instructions, machine learning methods and circuitry can include deriving a model from example inputs (such as a training set) and then making data-driven predictions.

Machine learning is related to optimization. Some problems can be expressed in terms of minimizing a loss function on a training set, where the loss function describes the disparity between the predictions of the model being trained and observable data.

Machine learning tasks can include unsupervised learning, supervised learning, and reinforcement learning. Approaches to machine learning include, but are not limited to, decision trees, linear and quadratic classifiers, case-based reasoning, Bayesian statistics, and artificial neural networks.

Neural Networks—https://patents.google.com/patent/US9697463

This specification relates to computing neural network inferences in hardware.

Neural networks are machine learning models that employ one or more layers of models to generate an output, e.g., a classification or generation, for a received input. Some neural networks include one or more hidden layers in addition to an output layer. The output of each hidden layer is used as input to the next layer in the network, i.e., the next hidden layer or the output layer of the network. Each layer of the network generates an output from a received input in accordance with current values of a respective set of parameters.

Neural networks generally comprised of various permutations of several different architectures, including but not limited to Convolutional Neural Networks (CNNs), Recurrent Neural Networks (RNNs), or Graph Neural Networks (GNNs). These network architectures are chosen according to the objective of the network and the structure of the input and output tensor matrices. These architectures can be combined to form larger networks, including Generative Adversarial Networks (GANs), Variational AutoEncoders (VAEs), and others.

Each neural network layer has an associated set of kernels. Each kernel includes values established by a neural network model created by a user. Kernels can be represented as a matrix structure of weight inputs.

One way of computing weight calculations requires numerous matrix multiplications in a large dimensional space. A processor can compute matrix multiplications through a brute force method. For example, although compute-intensive and time-intensive, the processor can repeatedly calculate individual sums and products for convolution calculations. The degree to which the processor parallelizes calculations is limited due to its architecture.

Variational AutoEncoders

An AutoEncoder is a type of artificial neural network structure which is designed to learn the features required to compress high dimensional data elements down low-dimensional latent representations, also referred to as codes, or latent variables, before subsequently uncompressing that data to a reconstructed original domain. It comprises an encoder, to compress the data, a latent variable that represents the low-dimensional code of the data, and a decoder, which uncompresses the data back to the original form.

Variational AutoEncoders are a subclass of AutoEncoders where a specific set of assumptions are made about the distribution of data, resulting in an additional loss component. Unlike an AutoEncoder, a Variational AutoEncoder learns the probability distribution representing the data, leading to a regularized distribution of encoded latent variables within a manifold, herein called the "latent space manifold". This results in the latent representations of similar inputs being located close to each other within the latent space manifold.

Chemical and Catalyst Features

The term "chemical features" is employed herein in relation to input reactants and the output product. Specifically, the chemical features of the input reactants are those features or characteristics that determine or influence how they react to product an output product (or products) in a chemical reaction. The chemical features of the output product(s) are those features or characteristics that determine or influence how they are produced in a chemical reaction. The chemical features can comprise properties (chemical and/or physical) or behaviour of individual atoms, compounds, or molecules, reactions, etc., such as, but not limited to, atom type, bonds & bond type, polarity, geometric configuration, physical properties, spherical harmonic and quantum mechanical properties. Preferred chemical features are one or more of atom type, valence/orbital hybridization, bond type, polarity, aromaticity, atomic number, arrangement of atoms, hydrogen count, conjugation, coulomb repulsion, bond distance, atom number, reaction mapping (if applicable) and Haldane relationships. More preferably the chemical features of the input reactants and/or the output product(s) comprise or consist of atom type, bond type, and arrangement of atoms, i.e. molecular geometry.

The first data set from which the machine learning models described herein learn is comprised of these chemical features. Similarly, the operating feature set used by the computer system described herein defines the input reactants and the output product(s) in terms of these chemical features.

The term "catalytic activator" employed herein means an agent which will interact with or bind to chemical features/one or more input reactants and/or lower the activation energy of a chemical reaction. The catalytic activator may be inorganic or organic, and may be a catalyst, or an antibody. Preferably the catalytic activator is a catalyst. More preferably the catalyst is an enzyme. Enzymes are comprised of one or more chains of amino acids, and have primary, secondary, and tertiary structures which determine their properties such as specificity and catalytic capability.

The features of the structure or composition of the catalytic activator (which is preferably a catalyst) are also referred to herein as "catalyst features" and may include one or more of atom type, bond type, arrangement of atoms, i.e. molecular geometry, or amino acid or nucleic acid sequence or their spatial arrangement. As indicated above, the catalyst is preferably an enzyme and the "catalyst features" are preferably the sequence of amino acids, and/or their spatial arrangement, The second data set—the data set from which the machine learning models described herein learn—is comprised of these catalytic activator features. Similarly, the trained machine learning model of the computer system described herein generates a set of these catalytic activator features.

Data used for training can be obtained from suitable databases available in the art, e.g., KEGG (https://www.ge-nome.jp/kegg/), UniParc database, and the Zinc database.

The operating feature set defining chemical features of the input reactants and the chemical features of the output products of a reaction, and the first and second sets of training data, may be received by the model as a molecular or chemical graph e.g., as a Networkx graph. The representation of chemical molecules by molecular or chemical graphs is known (https://en.wikipedia.org/wiki/Molecular_graph). Further, a script to convert rdkit molecules to Networkx graphs is provided in the software store GitHub.

Referring to FIG. 1, input data 100 is provided to an importer 101 which formats the input data into a representation which can be converted to a tensor by 102, producing a feature vector 103. This feature vector is encoded by 106. The encoder 106 comprises a set of nodes in an input layer 116, each node in the input layer being connected to one or more nodes of a hidden layer 117. Each node of the hidden layer 117 is connected to one or more nodes of an output layer 118 in a multi-layered neural network. The function of each node is parameterised by one or more respective parameters, e.g. weights. During a learning stage the aim is, based on a set of input training data 102, to find values for the various parameters such that the graph as a whole would generate a desired output for a range of possible inputs. Over multiple iterations of forward and backward propagation through the network, the parameters are gradually tuned to decrease their errors, and the neural network converges to a solution. In a subsequent stage, the thus trained model can be used to make predictions of outputs given specified set of inputs or to make inferences as to inputs given the specified set of outputs. The model should also generalize to accurately infer or predict inputs and outputs on which it has not been trained. In the Variational AutoEncoder (VAE) described herein, the learned output of the encoder is a latent vector in a latent representation space 107. A decoder 108 similarly constructed as a multilayered neural network, has an input layer 119 (in this the input layer receives a latent vector representation from the latent representation space 107) a hidden layer 120 and an output layer 121. In this case the output layer delivers a reconstructed feature vector 109 which can be converted to the original tensor format (or an alternative format) 114. The output tensor 114 can be converted to any suitable representation 115. The reconstructed feature vector 109 is compared with the input feature vector 103 using a similarity metric 111. The output of the similarity metric 111 is fed to a loss function 112. The input feature vector 103 is also compared with encoded latent vectors in the latent space 107 to produce the Kullback-Leibler (KL) divergence 110, a measure of the information lost when between the feature vector representation in 103 and the latent representation in 107. The KL divergence to the loss function 112. The output of the loss function 112 controls backpropagation 113, which is itself controlled by an optimizer function, which can update the weights of the neural network layers of the encoder and the neural network layers of the decoded as indicated diagrammatically.

FIG. 1 represents a single domain Variational AutoEncoder, for example for amino acids sequences. It can be trained to encode amino acid sequences provided in the input data into a continuous representation in the latent space in the knowledge that that continuous representation can be accurately decoded into the original amino acid sequence.

Figure 2A:
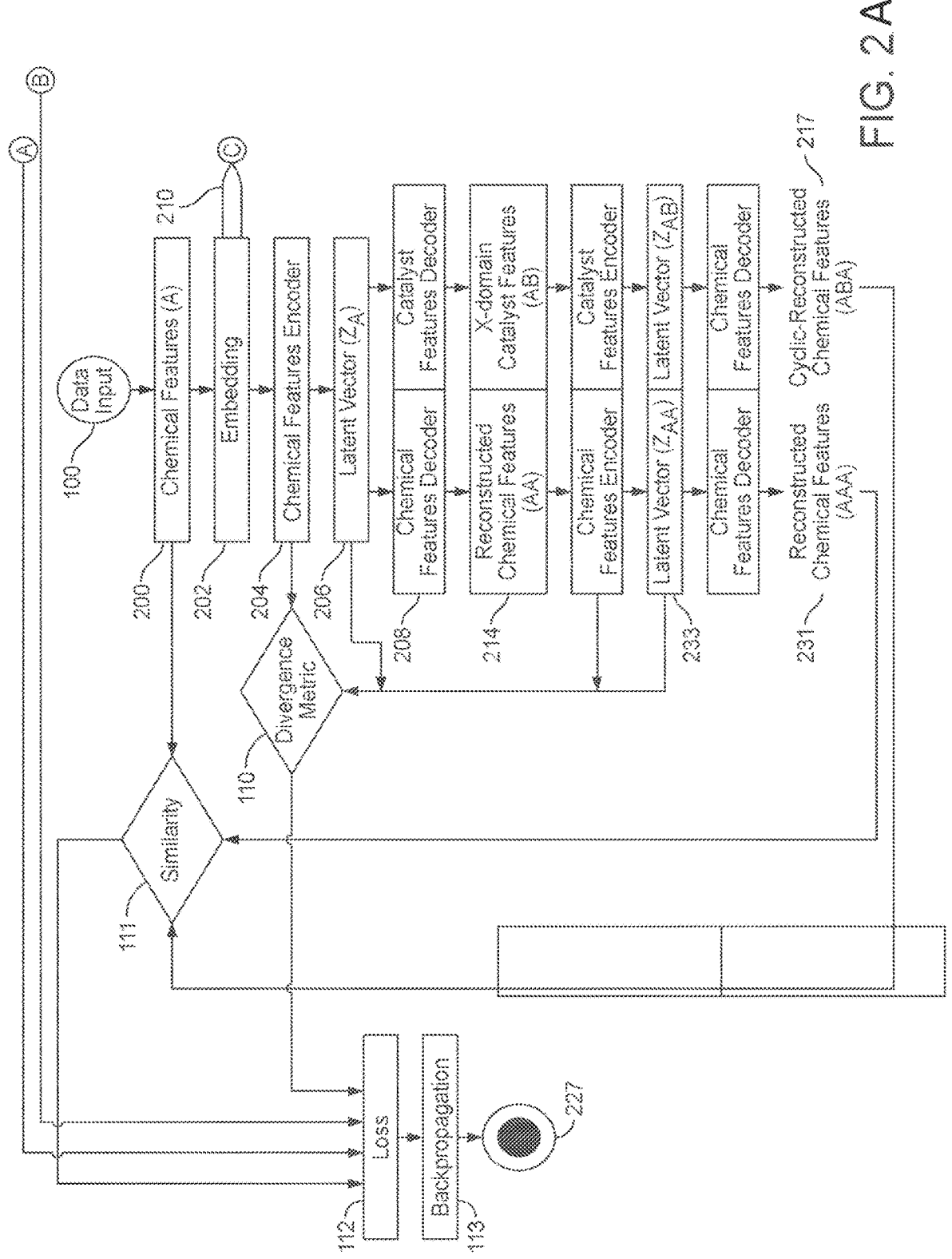
FIG. 2 High-level depiction of the components of a Variational AutoEncoder for generating a jointly distributed latent manifold for molecule to amino acid sequence translation.
Figure 2B:
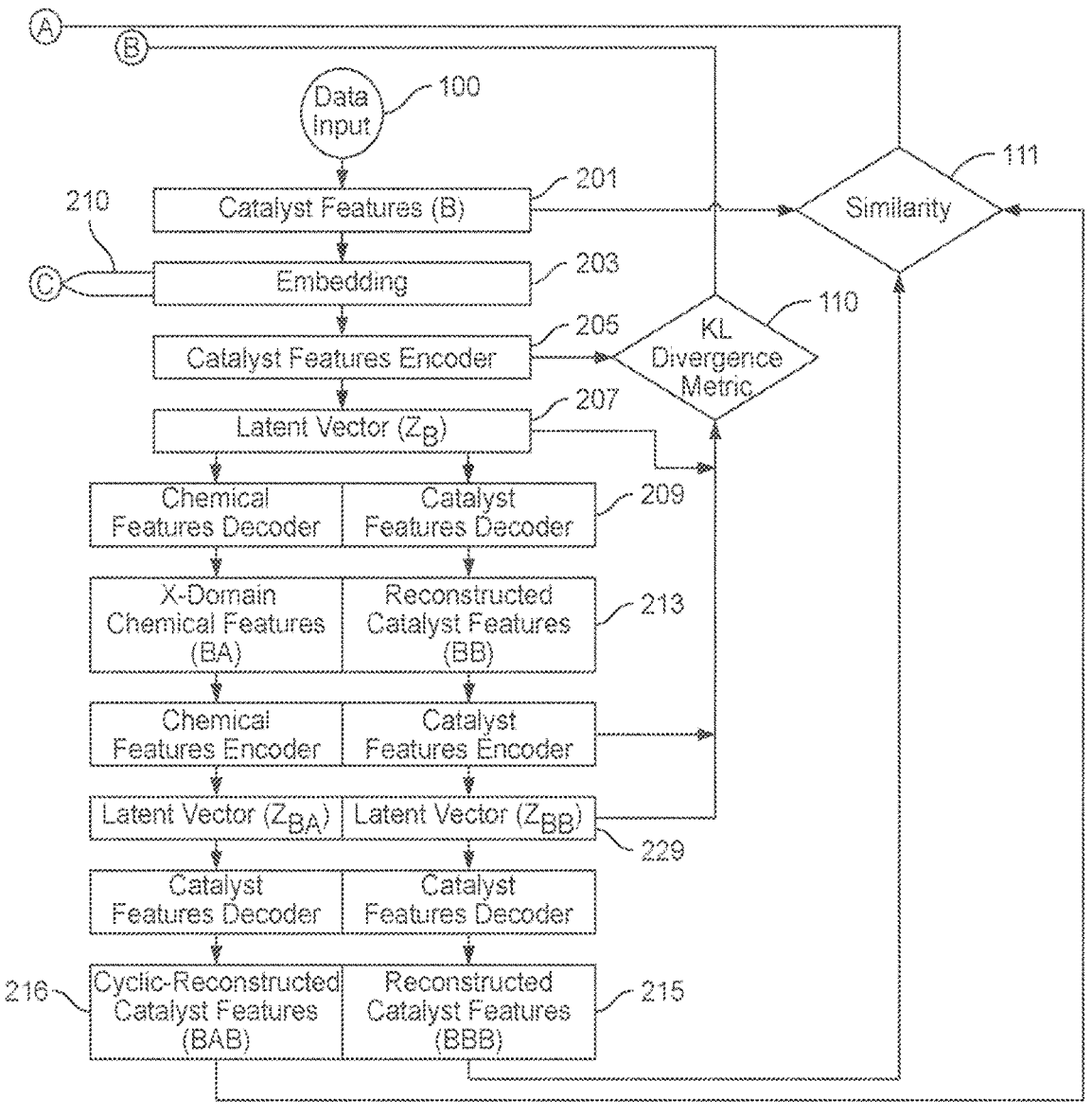

FIG. 2 depicts a Variational AutoEncoder which enables encoding and decoding in two domains simultaneously so that suitable catalysts can be generated for particular known reactions between target input reactant(s) and output product molecule(s). The joint domain Variational AutoEncoder comprises two single domain Variational AutoEncoders. A chemical domain Variational AutoEncoder comprises components as described in FIG. 1. That is, input data 100 is converted into chemical feature vectors 200 to be supplied to a chemical features encoder 204. The embedded chemical features vector is used to generate part of the KL divergence metric 110. The latent vector from the chemical latent representation space 206 is also supplied to generate the KL divergence metric 110 as well as to the chemical features decoder 208.

The reconstructed chemical features 214 are re-encoded by the chemical features encoder and supplied to generate the KL divergence metric 110. A new latent vector is formed of the encoded reconstructed chemical features and this is also supplied to generate the KL divergence metric 110. The new latent vector is supplied again to the chemical features decoder and the reconstructed chemical features are applied to a similarity metric 211 where they are compared with the original chemical features and the output supplied to a loss function 112 which controls backpropagation 113 and eventually producing a set of trained model weights 227.

Before describing the second path in the chemical domain, it is noted that there is a corresponding set of modules for a catalyst domain Input catalyst data 100 is converted to catalyst features 201 which are embedded into a catalyst feature vector 203 to supply to a catalyst feature encoder 205. The catalyst features are then treated in the same way in the catalyst domain as the chemical features were treated in the chemical domain using a catalyst KL divergence metric 110 and the similarity metric 111. These metrics can be separate from or the same as their corresponding chemical KL and similarity metrics in the chemical domain.

In addition to its primary domain, each Variational Auto-Encoder has a secondary path which enables the cross-over into a second domain. The chemical features latent vector 206 is supplied to the catalyst feature decoder 209 which generates X-Domain catalyst features which are referenced AB, because they are now a translation from the chemical features domain "A" to the catalyst features domain "B". That is, the chemical feature vector has been decoded into the catalyst domain. These X-Domain catalyst features are supplied to the catalyst features encoder 205 to generate a latent vector $Z_{AB}$. The latent vector is supplied to the chemical features decoder to generate cyclic-reconstructed chemical features ABA 217 which are now applied to the similarity metric 111 in the chemical domain.

A similar process takes place in the catalyst domain. That is, the latent catalyst feature vector is decoded using the chemical features decoder 208 to generate X-Domain chemical features BA. These are applied to the chemical features encoder 204 to generate a latent vector $Z_{BA}$ which is decoded by the catalyst features decoder 209 to generate cyclic-reconstructed catalyst features BAB. These are applied to the similarity metric 111 in the catalyst domain.

Figure 3:
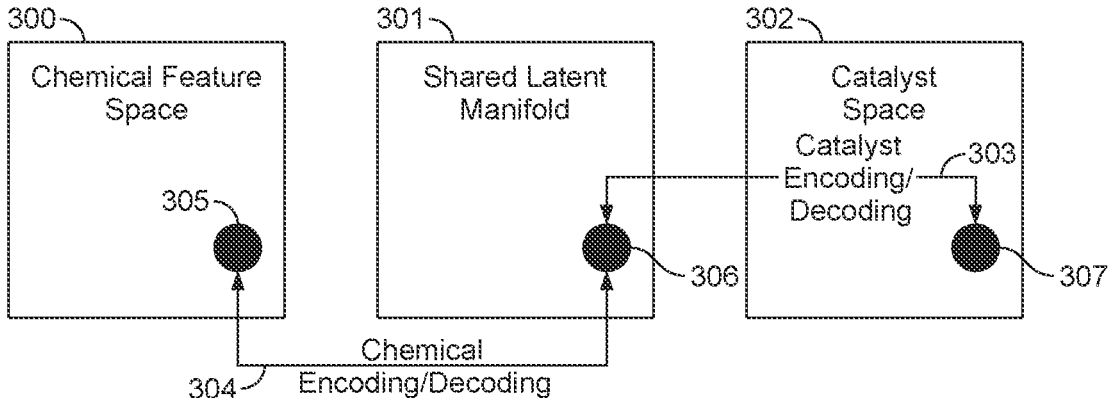
FIG. 3 High-level generalized depiction of the meta-architecture of the jointly distributed variational autoencoder.

FIG. 3 schematically illustrates the meta architecture of the structure of FIG. 2. A chemical feature space 300 comprises chemical features. These chemical features can represent reactions in the form of the features of input reactants and output products, individual chemicals, or both reactions and chemicals.

Chemical features of the chemical feature space 300 are encoded into the latent manifold (latent space) 301 from which they can be decoded back into the chemical feature space using the chemical domain Variational AutoEncoder represented by reference numeral 304 in FIG. 3. The chemical domain Variational AutoEncoder can be trained to optimise the representation in the latent space 301 such that it can be accurately decoded back to the original features. A catalyst feature space 302 can similarly be encoded into the latent space 301. In this way, the latent space becomes a shared, or jointly distributed latent space. Reference numeral 303 diagrammatically denotes the catalyst domain Variational AutoEncoder which is trained to encode and decode the catalyst features to provide the most accurate representation in the shared latent space. The distribution of the latent vectors in the chemical domain and the catalyst domain in the shared latent space is controlled such that a reaction point encoded into the shared latent space from the chemical feature space corresponds to a suitable catalyst for that reaction in the catalyst space.

Figure 4:
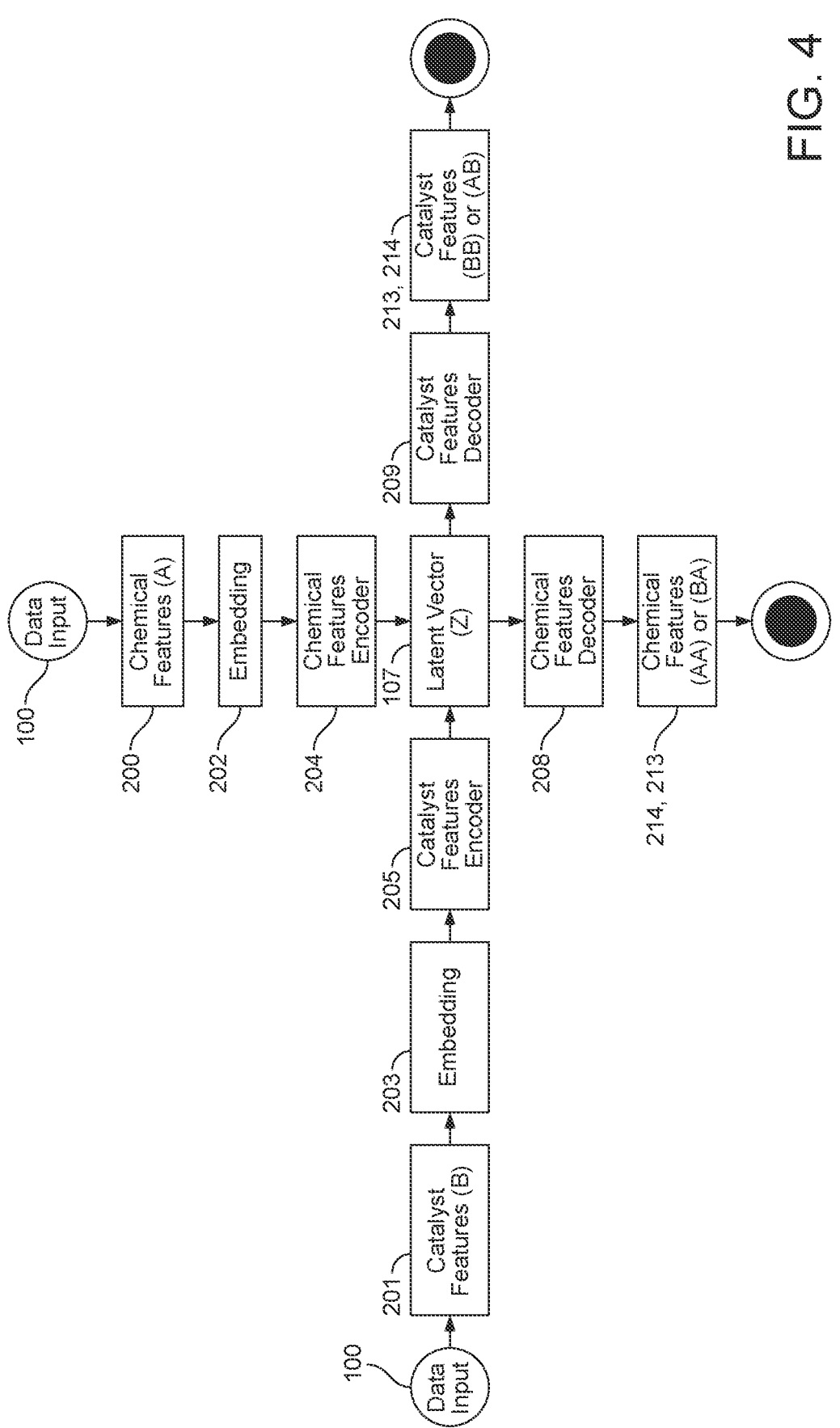
FIG. 4 Flow of processing representations from two domains on a trained model.

FIG. 4 shows the flow of processing representations from the two domains on a trained model. The trained model can be used to generate catalyst features from input chemical features, or chemical features from input catalyst features. In the former flow, input data 100 is converted to chemical features 200 which are embedded 202 into a chemical feature vector applied to the chemical feature encoder 204. The chemical features are encoded into latent vectors 107 in the latent vector space, and the latent vectors are applied to the catalyst decoder 209 which decodes catalyst features (BB or AB) to generate suitable catalyst 214. Alternatively, input catalyst data 100 can be used to provide catalyst features 201 which are embedded 203 into a catalyst feature vector applied to catalyst features encoder 205. The catalyst features are encoded into a latent vector (Z) in the latent vector space 107. The latent vectors are decoded using the chemical features decoder 208 to generate chemical features (AA) or (BA) 413 from which chemicals 214 can be derived.

FIG. 5 shows an example of a generated catalyst, here an amino acid sequence, 500 constructed from a set of chemical features 501. A catalyst 500 can also be used to generate a set of reaction features 501. Analysis of the generated amino acid sequence, 500, by alignment with the sequence of the enzyme glucose oxidase which is used to catalyse the oxidation of glucose to hydrogen peroxide and D-glucono-1,5-lactone, (e.g. with blast alignment at https://blast.ncbi.nlm.nih.gov/Blast.cgi?PROGRAM=blastp&PAGE_TYPE=BlastSearch&LINK_LOC=blasthome) demonstrates that this generated sequence, 500, has around 50-60% sequence identity with the sequence of glucose oxidase.

In a preferred arrangement of the invention, the network is structured such that the Variational AutoEncoders encode identical latent vectors within the latent space manifold. For example, a set of chemical features describing a reaction encoded to a specific point within the latent space manifold using the chemical encoder should decode to a molecular structure or a catalytic activator (e.g. the amino acid sequence of an enzyme) that will catalyze that reaction using a sequence decoder sampled from the same latent vector and vice-versa. For a given reaction which is encoded and decoded to a set of catalyst features, that catalyst should also encode and decode to the original chemical features.

If we define X as the data we want to model, z as the latent variable, P(X) as the probability distribution of data, P(z) as the probability distribution of the latent variable, P(X|z) as the probability distribution of generating data given the latent variable (the decoder), and Q(z|X) as the probability distribution of generating the latent variable given the original data (the encoder) X, then we can use the KL divergence metric, DKL, to generate an objective function for an individual Variational AutoEncoder, which can be expressed as:

$$\log P(X) - D_{KL}[Q(z|X)\|P(z|X)] = E[\log P(X|z)] - D_{KL}[Q(z|X)\|P(z)] \quad (1)$$

9

10

For each Variational AutoEncoder, the relevant features are fed through the model from the training dataset such that the loss for this objective function is found such that backpropagation can be performed in order to adjust the weights on the Variational AutoEncoder's computational graph such that this objective function is maximized.

In order to jointly solve for two latent space manifolds, cyclic reconstruction and/or weight sharing can be employed. During Cyclic Reconstruction, features from domain 1 are encoded to a latent vector, which is then decoded into a set of domain 2 features. These features are then re-encoded into a latent vector before being decoded back into their original domain 1. These features can then be compared directly with the ground truth features from the dataset as a part of the loss function. This can be augmented by sharing weights on the tensors in the embedding layers of both Variational AutoEncoders.

A preferred embodiment of the latent space conformation can be expressed as jointly solving the learning problems of two Variational AutoEncoders for the chemical and catalyst reconstruction, translation, and cycle-reconstruction.

If we define L as loss, E1 as the encoder for domain 1, the chemical features describing a reaction, and D1 as the corresponding decoder for domain 1, and E2 as the encoder for domain 2, the catalyst, and D2 as the corresponding decoder for domain 2, we can train both encoders and decoders simultaneously:

$$\min_{E_1, E_2, D_1, D_2} = \tag{2}$$

$$L_{VAE_1}(E_1, D_1) + L_{CC_1}(E_1, E_2) + L_{VAE_2}(E_2, D_2) + L_{CC_2}(E_2, E_1)$$

Here variational autoencoding within the same domain is represented as LV AEx and variational autoencoding cross domain is represented as LCCx, which refers to cyclic reconstruction. By encoding from an original domain, decoding to a new domain, re-encoding from the new domain, and re-decoding to the original, the loss between original data and the reconstructed original data can be found while training all networks.

We refer to the first equation as (1) and the second as (2).

The objectives of equation (2) may be solved by encoding, decoding, re-encoding, and re-decoding from one domain to the other.

It will thus be seen that the objects set forth above, among those made apparent from the preceding description, are efficiently attained and, because certain changes may be made in carrying out the above method and in the construction(s) set forth without departing from the spirit and scope of the invention, it is intended that all matter contained in the above description and shown in the accompanying drawings shall be interpreted as illustrative and not in a limiting sense.

It is also to be understood that the following claims are intended to cover all of the generic and specific features of the invention herein described and all statements of the scope of the invention which, as a matter of language, might be said to fall therebetween.

What is claimed:

1. A computer system for generating the molecular structure of a catalytic activator for a reaction in which input reactants are converted into an output product, the computer system comprising:
   one or more processors; and
   a non-transitory computer readable medium storing a plurality of instructions, which when executed, cause the one or more processors to:
   receive, by a trained machine learning model, an operating feature set defining chemical features of the input reactants and chemical features of the output product of a reaction, the trained machine learning model being a Variational AutoEncoder comprising: i) a chemical encoder configured to encode the chemical features into a latent vector that defines a point in a latent manifold space, and ii) a catalyst decoder configured to decode the defined point in the latent space into a latent vector defining the set of catalyst features for catalysing the reaction that converts the input reactants to the output product;
   generate, by the trained machine learning model, a set of catalyst features defining one or more catalytic activators for catalysing a reaction to convert the input reactants to the output product; and
   cause the reaction to convert the input reactants to the output product using the generated set of catalyst features defining one or more catalytic activators.

2. The computer system according to claim 1, wherein the machine learning model is a Variational AutoEncoder comprising a catalyst encoder operable to encode the catalyst features into a latent vector which defines a point in a latent space and a chemical decoder operable to decode the defined point in the latent space into a latent vector which defines the chemical features of the input reactants and output product of a reaction.

3. The computer system according to claim 1, wherein the encoders and decoders each comprise a neural network having an encoder comprising an input layer of nodes, at least one hidden layer of nodes and an output layer of nodes, the function of each node being parameterised by weights.

4. The computer system according to claim 1, wherein the trained machine learning model comprises kernel memory in which the weights are stored.

5. A method of training a Variational AutoEncoder machine learning model, the method comprising:
   providing a first set of training data defining chemical features of input reactants and output products for each of a plurality of reactions;
   encoding the chemical features into latent vectors defining points in a latent space and defining the distribution of the latent vectors in the latent space, wherein defining the distribution of the latent vectors in the latent space comprises:
   decoding the chemical latent vectors using a catalyst decoder to generate catalyst features in a catalyst domain,
   comparing the decoded catalyst features with catalyst features of the second set of training data,
   decoding the catalyst latent vectors using a chemical decoder into chemical features in a chemical domain,
   comparing the decoded chemical features with the chemical feature of the first set of training data, and
   minimising, jointly, a loss function in the comparison steps to match the distributions in the common latent space of the latent vectors in the chemical domain and the latent vector in the catalyst domain;
   providing a second set of training data defining catalyst features of catalytic activators for each of the plurality of reactions; and encoding the catalyst features into catalyst latent vectors in the latent space and matching the distribution of the catalyst latent vectors to the chemical latent vectors such that decoding a chemical latent vector at a point in the latent space generates catalyst features of a catalytic activator for catalysing a reaction to convert the input reactants of that reaction to an output product, the input reactant and the output product defined by the chemical features encoded in the latent vector.

6. The method according to claim 5, comprising the step of decoding the chemical latent vectors using a chemical decoder and comparing the decoded chemical features with the chemical features of the first set of training data and minimising the loss of an objective training function by adjusting weights in a first domain of the variational auto-encoder; and decoding the catalyst latent vector into decoded catalyst features and comparing the decoded catalyst features with catalyst features of the second set of training data to minimise the loss of an objective training function by adjusting weights of a second domain of the variational autoencoder, and sharing the weights of the first and second domains.

7. The computer system according to claim 6, wherein the encoders and decoders each comprise a neural network having an encoder comprising an input layer of nodes, at least one hidden layer of nodes and an output layer of nodes, the function of each node being parameterised by weights.

8. The computer system according to claim 5, wherein the catalytic activator is a catalyst.

9. The computer system according to claim 8, wherein the catalyst is an enzyme.

10. A computer program product, comprising a non-transitory computer-readable medium having computer-readable program code embodied therein to be executed by one or more processors, the program code including instructions to:

provide a first set of training data defining chemical features of input reactants and output products for each of a plurality of reactions;

encode the chemical features into latent vectors defining points in a latent space and defining the distribution of the latent vectors in the latent space, wherein defining the distribution of the latent vectors in the latent space comprises:

decode the chemical latent vectors using a catalyst decoder to generate catalyst features in a catalyst domain, compare the decoded catalyst features with catalyst features of the second set of training data, decode the catalyst latent vectors using a chemical decoder into chemical features in a chemical domain, compare the decoded chemical features with the chemical feature of the first set of training data, and minimize, jointly, a loss function in the comparison steps to match the distributions in the common latent space of the latent vectors in the chemical domain and the latent vector in the catalyst domain;

provide a second set of training data defining catalyst features of catalytic activators for each of the plurality of reactions; and encode the catalyst features into catalyst latent vectors in the latent space and matching the distribution of the catalyst latent vectors to the chemical latent vectors such that decoding a chemical latent vector at a point in the latent space generates catalyst features of a catalytic activator for catalysing a reaction to convert the input reactants of that reaction to an output product, the input reactant and the output product defined by the chemical features encoded in the latent vector.

11. The computer program product according to claim 10, wherein the program code further includes instructions to:

decode the chemical latent vectors using a chemical decoder and compare the decoded chemical features with the chemical features of the first set of training data and minimize the loss of an objective training function by adjusting weights in a first domain of the variational autoencoder; and decode the catalyst latent vector into decoded catalyst features and compare the decoded catalyst features with catalyst features of the second set of training data to minimize the loss of an objective training function by adjusting weights of a second domain of the variational autoencoder, and sharing the weights of the first and second domains.

12. The computer program product according to claim 10, wherein the program code further includes instructions to:

decode the chemical latent vectors using a chemical decoder and compare the decoded chemical features with the chemical features of the first set of training data and minimize the loss of an objective training function by adjusting weights in a first domain of the variational autoencoder; and decode the catalyst latent vector into decoded catalyst features and compare the decoded catalyst features with catalyst features of the second set of training data to minimize the loss of an objective training function by adjusting weights of a second domain of the variational autoencoder, and share the weights of the first and second domains.

13. A computer program product for generating the molecular structure of a catalytic activator for a reaction in which input reactants are converted into an output product, computer program product comprising a non-transitory computer-readable medium having computer-readable program code embodied therein to be executed by one or more processors, the program code including instructions to:

receive, by a trained machine learning model, an operating feature set defining chemical features of the input reactants and chemical features of the output product of a reaction, the trained machine learning model being a Variational AutoEncoder comprising: i) a chemical encoder configured to encode the chemical features into a latent vector that defines a point in a latent manifold space, and ii) a catalyst decoder configured to decode the defined point in the latent space into a latent vector defining the set of catalyst features for catalysing the reaction that converts the input reactants to the output product;

generate, by the trained machine learning model, a set of catalyst features defining one or more catalytic activators for catalysing a reaction to convert the input reactants to the output product; and cause the reaction to convert the input reactants to the output product using the generated set of catalyst features defining one or more catalytic activators.

14. The computer program product according to claim 13, wherein the machine learning model is a Variational Auto-Encoder comprising a catalyst encoder operable to encode the catalyst features into a latent vector which defines a point in a latent space and a chemical decoder operable to decode the defined point in the latent space into a latent vector which defines the chemical features of the input reactants and output product of a reaction.

15. The computer program product according to claim 13, wherein the encoders and decoders each comprise a neural network having an encoder comprising an input layer of nodes, at least one hidden layer of nodes and an output layer of nodes, the function of each node being parameterised by weights.

16. The computer program product according to claim 13, wherein the trained machine learning model comprises kernel memory in which the weights are stored.

\* \* \* \* \*